United States Patent [19]

Krauter et al.

[11] Patent Number: 5,359,994
[45] Date of Patent: Nov. 1, 1994

[54] PROXIMAL STEERING CABLE ADJUSTMENT

[75] Inventors: Allan I. Krauter, Syracuse; Robert L. Vivenzio, Auburn, both of N.Y.

[73] Assignee: Welch Allyn, Inc., Skaneateles Falls, N.Y.

[21] Appl. No.: 185,515

[22] Filed: Jan. 24, 1994

[51] Int. Cl.⁵ .............................................. A61B 1/00
[52] U.S. Cl. ........................................... 128/4; 604/95
[58] Field of Search .......................... 128/4, 5, 6–11, 128/656, 657, 658; 604/280, 95

[56] References Cited

U.S. PATENT DOCUMENTS

| | | | |
|---|---|---|---|
| 4,203,430 | 5/1980 | Takahashi | 128/4 |
| 4,294,233 | 10/1981 | Takahashi | 128/4 |
| 4,483,326 | 11/1984 | Yamaka et al. | 128/4 |
| 4,941,454 | 7/1990 | Wood et al. | 128/4 |
| 5,299,559 | 4/1994 | Bruce et al. | 128/4 |

FOREIGN PATENT DOCUMENTS 9200696  1/1992  WIPO ........................... 128/4

Primary Examiner—Stephen R. Crow
Assistant Examiner—John P. Leubecker
Attorney, Agent, or Firm—Harris Beach & Wilcox

[57] ABSTRACT

A steering control unit for a cable-actuated bending neck of an elongated probe has a cable slack adjustment mechanism disposed on the proximal end of the unit. This permits field service of the probe and allows for a watertight housing. The adjustment mechanism employs hollow adjuster screws that are threaded into the proximal side of the toothed racks of the control unit. Rack travel adjustment is also accomplished using hollow adjusting screws.

6 Claims, 3 Drawing Sheets

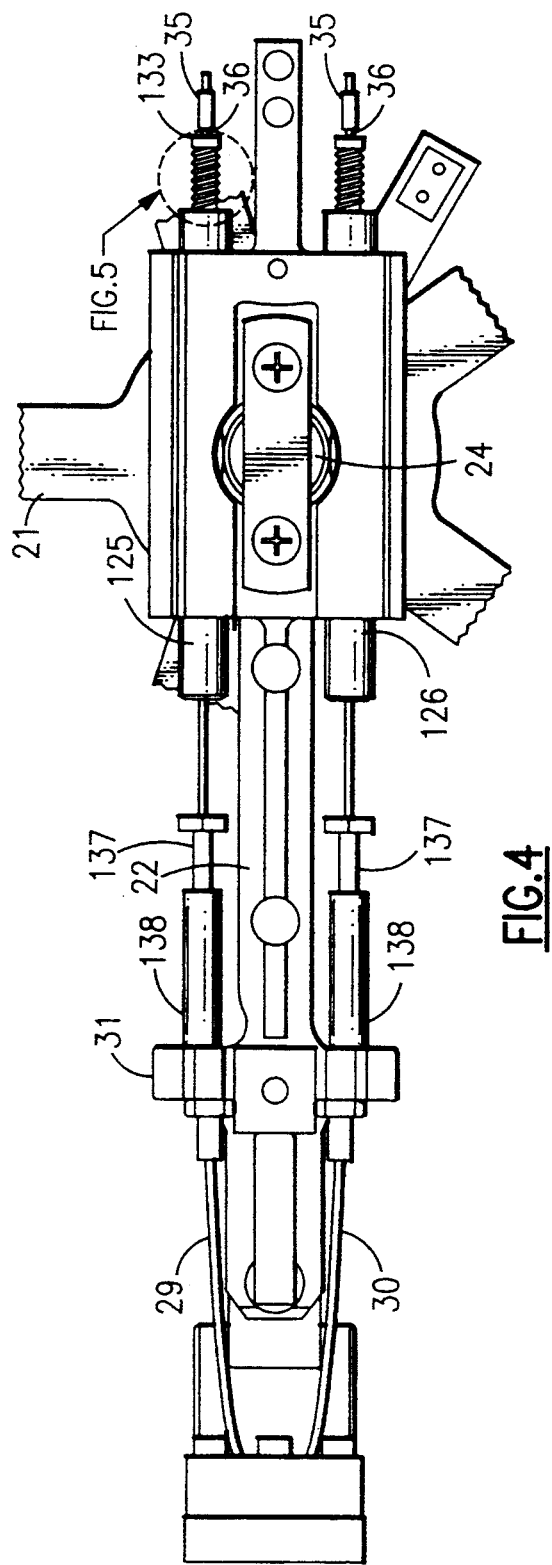
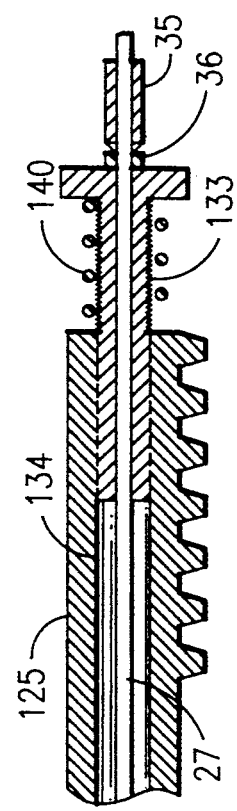
FIG.4
FIG.5

PROXIMAL STEERING CABLE ADJUSTMENT

BACKGROUND OF THE INVENTION

This invention relates to elongated probes such as borescopes and endoscopes, of which the distal end or tip is controllably bendable from a control mechanism at a proximal end of the probe. The invention is more specifically concerned with a technique for adjusting cable tension of a cable-type steering section.

In a steerable probe of this type, a manually actuated knob or handle on the control housing is rotated to effect differential movement of a pair of steering cables that extend forward, or distally, to the bendable steering section on the probe tip.

After a period of use, steering cables tend to develop slack. This slack reduces steering response of the bending or steering section, especially when the probe is in a straight-ahead orientation. This causes the probe tip to become floppy and unresponsive. For conventional cable steering systems, slack requires return of the probe or scope to the factory for repair.

Accordingly, there has been a need to provide for simple field adjustment of slack in the steering mechanisms of these probes.

OBJECTS AND SUMMARY OF THE INVENTION

Accordingly, it is an object of this invention to provide a cable type steering mechanism which permits the steering cables to be easily adjusted in the field.

It is another object to provide a field cable slack adjustment that is compatible with a watertight cover or housing for the control mechanism.

It is a further object to provide a slack adjustment mechanism that is equally applicable with two-cable and four-cable steering systems.

According to an aspect of this invention, a proximal cable adjustment is incorporated into a steering control mechanism for a cable-actuated steering or bending section of an elongated probe. In this type of probe for each of vertical and horizontal steering directions there is a pair of steering cables that are moved differentially to effect steering or bending. Each steering cable has a cable sheath that is substantially incompressible axially; that is, after all axially separated coils have closed, the sheaths strongly resist further axial compression. The steering control mechanism itself comprises a frame and a pinion or toothed wheel supported on the frame for rotation. For each pair of cables there is a pair of racks that are slidably held in the frame for proximal-distal motion. Each of the racks has an axial passage through which the respective cable passes. Teeth on the racks engage the toothed wheel. First and second cable sheath terminators are attached to the frame distally of the racks and the ends of the respective cable sheaths are secured in these. The cables each have a cable terminator, e.g., an enlarged plug, affixed onto its proximal end. In this invention, there are cable adjusters disposed over the proximal part of each cable between the proximal end of the respective rack and the associated cable terminator. Each of these can be in the form of a hollow, axially slotted screw with a shaft that is screwed into the proximal end of the rack passage and a head that abuts the associated cable terminator.

Adjustment can be carried out easily from the proximal side of the mechanism, gaining access favorably by removing a plug or cover which can be resealed in place after adjustment. This is important in creating a watertight design for the housing of the steering control mechanism. A deep socket wrench can be used to tighten or loosen the cable adjustment screw. Also because slack adjustment occurs away from any exposed cable, cable kinking is less likely to occur.

A light anti-rotation spring is favorably disposed over the shaft of the cable adjustment screw between the proximal end of the rack and the head of the screw. This spring prevents rotation of the screw during use of the probe, but permits rotation of the screw for cable adjustment.

An axial slit along the screw, through both the shaft and head, allows the adjustment screw to be installed around the cable after the cable has been passed through the rack from the distal end.

Rack travel is controlled by other hollow screws which are threaded into the cable sheath terminators. The cables exit the sheath terminators through these screws. Rack travel is stopped when the rack contacts the head of the screw. Rack travel can be lengthened by threading the screw into the terminator, and can be shortened by threading the screw out of the terminator.

The above and many other objects, features and advantages of this invention will become apparent from the ensuing description of a preferred embodiment, to be read in conjunction with the accompanying Drawing.

BRIEF DESCRIPTION OF THE DRAWING

FIG. 4 is an elevation of a portion of a borescope steering control section according to an embodiment of this invention.

FIG. 5 is an enlargement of a cable adjustment provision of this embodiment, taken as indicated in FIG. 4.

DETAILED DESCRIPTION OF THE PREFERRED EMBODIMENT

Figure 1:
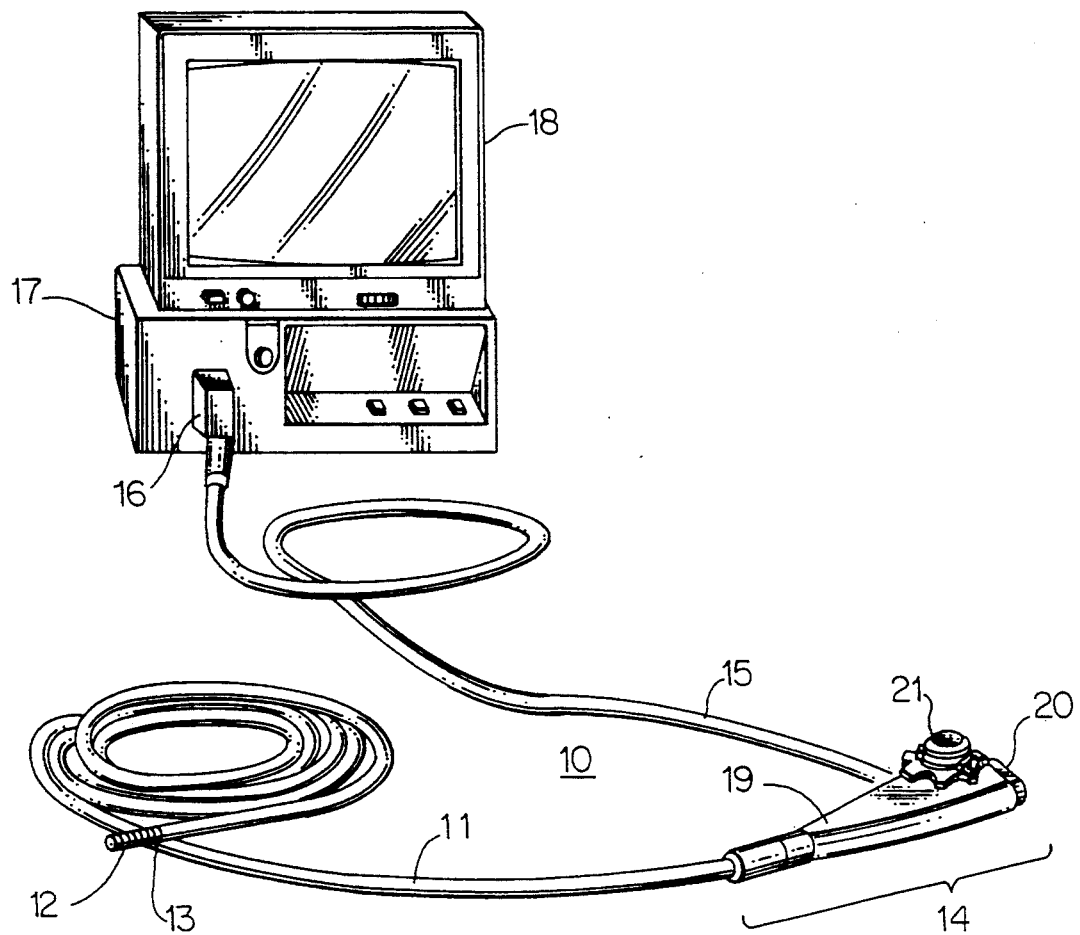
FIG. 1 is a perspective view of a borescope having a steerable bending neck.

With reference now to FIG. 1 of the Drawing, an endoscope or borescope 10, which here is an elongated optical or video probe, comprises an elongated flexible insertion tube 11. At a distal tip of the insertion tube 11 is a viewing head 12, which can employ a video imager. A remotely steerable bending neck 13 is situated adjacent the viewing head 12.

A control unit 14 is attached to a proximal end of the insertion tube 11 and connects by means of a flexible umbilical 15 and a connector module 16 to a video processor 17 which receives a video signal from the video imager in the head 12 and produces a video display on an associated monitor 18.

The control unit 14 has a housing 19. A rear or proximal panel 20 thereof is removable for access to cable adjustment screws, as described later.

A pair of handwheels 21 mounted on the housing 19 permit manual control of bending of the bending neck 13 in the vertical and horizontal direction, respectively. The two hand wheels connect to pinions of respective rack and pinion cable controls for differentially actuating respective pairs of control cables that extend forward through the insertion tube 11 to the bending neck 13.

In the following description, only the mechanism associated with a single pair of cables is illustrated and described. A similar mechanism, not shown, is associated with the other pair of steering cables.

A prior-art steering control mechanism, described with reference to FIGS. 2 and 3, can be situated within the housing 19 of the steering control unit 14. In this mechanism an elongated frame 22, here extending proximally-distally, has a rack-retaining portion 23 mounted on its proximal end. There is a pinion or toothed wheel 24 rotatably mounted on the frame within this portion 23. The pinion 24 is coupled to the handwheel 21 to rotate with it in either direction. A pair of racks 25, 26 move in opposite directions when the handwheel 21 and the pinion 24 rotate. These racks are slidably held in the rack-retaining portion 23 so that teeth on the racks engage the pinion 24. The racks 25,26 are respectively coupled to first and second cables 27,28 that extend forward through associated cable sheaths 29,30 to the bending neck 13. The cable sheaths are flexible but strongly resist compression, and each has its proximal end held in a respective cable sheath terminator 31,32. The two terminators 31,32 are affixed to the frame 22 on the distal side of the racks 25,26.

Figure 3:
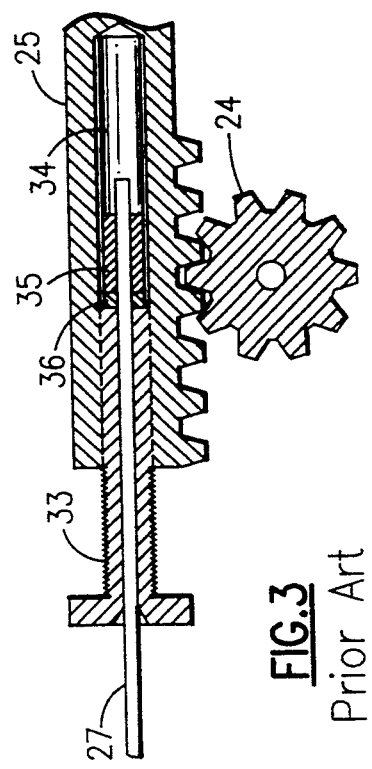
FIG. 3 is an enlargement of a cable adjustment provision shown here in cross section, taken as indicated in FIG. 2.

As shown in more detail in FIG. 3, the proximal end of each cable 27,28 is held in an associated hollow adjuster screw 33 which is threaded into a receptacle 34 at a distal end of the rack 25. In this prior design, the cable passes through the hollow core of the screw 33 and a cable terminator 35, secured to the end of the cable 27, extends proximally into the receptacle 34. A standard anti-jam washer 36 is interposed between the cable terminator 35 and the end of the shaft of the screw 33.

Shown on the proximal ends of the racks 25 and 26 are respective travel adjustment screws 37. In this version, these are solid screws. A rack plate 38 mounted at the proximal end of the frame 22 contacts the screws 37 to limit travel of the racks 25 and 26.

In this design, the adjustment screws 33, which are positioned rather forward in the control unit 14, are not easily accessible for adjustment by the user.

Although not shown in detail here, threadlockers are employed for the hollow screws 33 and the solid screws 37. These render the setting of each screw substantially permanent.

Because of the construction described above, adjustment of cable slack must be conducted at the factory, making adjustment of slack inconvenient and expensive.

Figure 6:
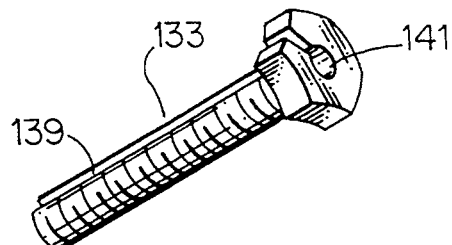
FIG. 6 is a perspective view of a slotted hollow adjustment screw employed in this embodiment.
Figure 2:
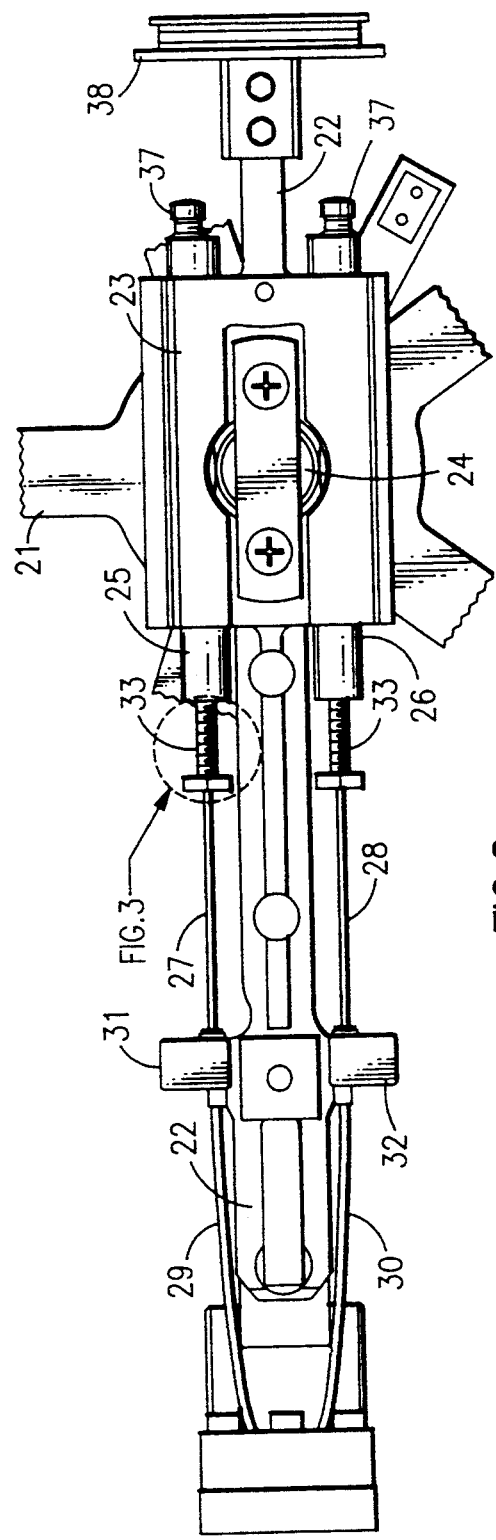
FIG. 2 is an elevation of a portion of a borescope steering control section of the prior art.

An embodiment of this invention, which overcomes the disadvantages of the prior art, is shown in FIGS. 4, 5, and 6, in which similar elements to those shown in FIGS. 2 and 3 are identified with the same reference numbers, and elements which are changed or reconfigured are identified with numbers raised by 100. A detailed description of the elements in common with FIGS. 2 and 3 will not be repeated.

As shown in FIGS. 4 and 5, the cables 27 and 28 pass entirely through longitudinal passages 134 in the racks 125 and 126, and are secured in hollow adjuster screws 133. These screws are threaded into the passages 134 at the proximal ends of the respective racks 125, 126. A terminator 35 and an anti-jam washer 36 on the cable 27 are disposed proximally of the screw 133 and abut the head of the screw 133. A light anti-rotation helical spring 140 is disposed over the shaft of the screw 133 and is compressed between the proximal end of the rack 125 or 126 and the head of screw. This spring 140 prevents selfrotation of the screw, but yields to permit adjustment when needed.

As shown in FIG. 6, an axial slit 139 can be provided in the adjusting screw 133 to allow the cable 27 or 28 to be inserted into its hollow interior 141. This allows the screw 133 to be installed around the cable after the cable 27 or 28 has been passed through the rack 125 or 126 from its distal end.

Also, to provide for ease of assembly and disassembly of the cables and sheaths from the probe, axial slits (not shown) can be provided in the frame. These permit the cable sheath terminators to be moved axially out of their respective sockets, and then radially out of the frame.

Returning to FIG. 4, rack travel adjustment is accomplished with hollow screws 137 that are disposed distally of the racks 125,126. Here the screws 137 are threaded into extensions 138 of the respective cable sheath terminators. Rack travel is stopped when the rack 125 or 126 contacts the head of the respective screw 137. Travel is increased by turning the threaded screw 137 into the respective terminator extension 138, and is decreased by turning the screw out of the respective terminator extension.

Adjustment of cable tension can be accomplished easily using a tool in the form of a hollow elongated tubular socket. The socket fits over the head of the adjuster screw 133 and also accommodates the terminator 35 and anti-jam washer 36. Screwing the adjuster screw out decreases cable slack while screwing the adjuster screw in increases cable slack. Each of the two or four adjuster screws 133 can be accessed by opening access ports (not shown) on the proximal end of the steering control housing 19, or in alternative embodiments by removing the rear access panel 20 such as that shown in FIG. 1. This construction enables the housing 19 to be made watertight.

While this invention has been described with reference to a preferred embodiment, the invention is not limited to that precise embodiment. Rather, many modifications and variations will present themselves to persons skilled in the art without departure from the scope and spirit of this invention, as defined in the appended claims.

We claim:

1. A steering mechanism for bending a cable-actuated steering section of an elongated probe of the type in which a pair of steering cables are moved differentially to effect the bending of the steering section, said cables having cable sheaths that are substantially incompressible axially, the steering mechanism comprising an elongated frame; a toothed wheel rotatably mounted on said frame; first and second racks slidably held in said frame for proximal-distal motion, each of said racks having an elongated passage through which a respective one of said cables passes and a set of teeth engaging said toothed wheel; cable sheath terminator means positioned on said frame distally of said racks for securing proximal ends of said cable sheaths; first and second proximal cable terminators affixed onto proximal ends of said cables, and first and second proximal cable adjuster means adjustably positioned on proximal ends of said first and second racks, respectively, and situated between the respective rack and associated proximal cable terminator for permitting adjustment of cable tension from the proximal end of the steering mechanism.

2. The steering mechanism according to claim 1 wherein said cable adjuster means include hollow screws over the respective cables, each said screw having a hollow shaft threadably engaged into the proximal end of the associated passage in the respective rack, and a head positioned against the associated cable terminator.

3. The steering mechanism according to claim 2 wherein each said hollow screw has an axial slot to permit the screw to be installed onto said cable.

4. The steering mechanism according to claim 3 wherein each said cable adjuster means also includes an anti-rotation helical spring positioned over the shaft of the hollow screw between said head and the proximal end of the associated rack.

5. The steering mechanism according to claim 1 further comprising first and second travel adjustment means disposed between said cable sheath terminator means and said racks for adjustably limiting travel of the respective racks.

6. The steering mechanism according to claim 5 wherein each said travel adjustment means includes a hollow screw disposed over the respective cable and adjustably threaded into a proximal portion of said cable sheath terminator means.

* * * * *